United States Patent [19]

Baker

[11] 3,953,478

[45] Apr. 27, 1976

[54] TETRAHYDROFURANYL BROMOACETATES BIOCIDES

[75] Inventor: Don R. Baker, Orinda, Calif.

[73] Assignee: Stauffer Chemical Company, Westport, Conn.

[22] Filed: Apr. 2, 1975

[21] Appl. No.: 564,517

[52] U.S. Cl............................. 260/347.4; 424/285; 71/88
[51] Int. Cl.²...................................... C07D 307/24
[58] Field of Search...................... 260/347.4, 347.5

[56] References Cited
UNITED STATES PATENTS
2,400,095    5/1946    Borglin ........................... 260/347.4

Primary Examiner—Harry I. Moatz
Attorney, Agent, or Firm—Daniel C. Block

[57] ABSTRACT

This invention relates to tetrahydrofuranyl bromoacetates having the formula

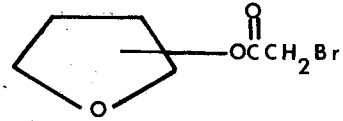

and to their utility as selective biocidal agents showing efficacy on bacteria, algae and fungi.

4 Claims, No Drawings

TETRAHYDROFURANYL BROMOACETATES BIOCIDES

DETAILED DESCRIPTION OF THE INVENTION

This invention relates to tetrahydrofuranyl bromoacetates having the formula

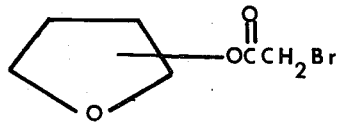

and to their utility as selective biocides when used in a biocidally effective amount. The term "selective biocide" as used herein refers to a compound which is useful for controlling the growth of selected bacteria, fungi, and algae. Controlling the growth of bacteria, fungi and algae by applying the compounds described herein can be accomplished by applying a biocidally effective amount to the environment in which the growth of bacteria, fungi and algae is encouraged. The compounds may be applied to any environmental area which supports the growth and development of bacteria, fungi and algae. By "controlling" is meant the prevention of the growth of the bacteria, fungi and algae to be controlled.

The compounds of this invention can be prepared by reaction of the suitable hydroxy tetrahydrofuran with bromoacetyl bromide to give the desired product. In the case of one of the compounds of the present invention, 3-hydroxy tetrahydrofuran is reacted with bromoacetyl bromide, both of which are commercially available, according to the procedure shown in the following example. Following this preparation example are examples of the utility of the resultant compound, 3-bromoacetoxy tetrahydrofuran, in controlling the growth of bacteria, fungi and algae.

EXAMPLE 1

3-bromoacetoxy tetrahydrofuran

In a four-neck, 2-liter flask, 42.5 g (0.48 mole) 3-hydroxy tetrahydrofuran was dissolved in 600 ml benzene. The resultant solution was cooled to below 20°C in an ice-water bath. 135.3 g (58.4 ml, 0.67 mole) bromoacetyl bromide was then added to the solution. 75.9 g (77.6 ml, 0.96 mole) pyridine was added dropwise to the solution over a 30-minute period. When the addition was complete, stirring was continued for 1 hour at the above temperature. The reaction mixture was then removed from the cooling bath and allowed to come to room temperature. The solution was first washed with 350 ml of water, then with 100 ml 1N HCl, and finally with 100 ml saturated $NaHCO_3$ solution. The remaining benzene solution was dried with $MgSO_4$ and filtered. The benzene solvent was removed by evaporation in vacuo, leaving the product oil. The yield was 70.1 g, or 69.9% of the theoretical yield of 100.3 g. The refractive index of the product was $n_D^{30} = 1.5022$. The structure of the product was confirmed by spectral evidence. Epichlorohydrin (1% by weight) was added as a stabilizer.

In the remainder of the examples, the compound of Example 1 will be referred to as Compound No. 1.

EXAMPLE 2

In Vitro Agar Screening Tests

This test measures the bactericidal, fungicidal and algaecidal properties of a compound when in contact with growing bacteria, fungi or algae in an artificial medium. The test is conducted by adding 20 ml portions of a suitable warm sterile agar solution into 20 × 100 mm Petri dishes at levels of 1, 5, 10 and 50 µg/ml and mixed with the warm mobile agar solution. The treated agar mixture is then allowed to come to room temperature and solidify. Cells of the chosen organism are streaked on the surface of the solidified agar and are then incubated for such lengths of time that untreated samples containing no toxicant show luxurious growth typical of the particular organism. This time varies from 24 hours to 1 week depending on the particular organism. The fungi are incubated at 30°C and the bacteria are incubated at 37°C. The algae are incubated at room temperature under artificial light. Nutrient agar is used as the medium in this test for the bacteria. Potato dextrose agar is used as the medium for the fungi with the exception of *Trichophyton mentagrophytes* for which Emmons agar is used. A modified Jack Meyers agar is used for the growth of the algae.

The extent of growth is noted at the end of the incubation period.

Representative organisms used in this test are as follows:

Bacteria
*Bacillus cereus*
*Brevibacterium ammoniagenes*
*Enterobacter aerogenes*
*Escherichia coli*
*Pseudomonas aeruginosa*
*Pseudomonas fluorescens*
Fungi
*Aspergillus fumigatus*
*Aspergillus niger*
*Aspergillus oryzae*
*Pencillium expansum*
*Pencillium ochra-chloron*
*Pencillium vermiculatum*
*Rhizopus stolonifer*
*Trichoderma sp.*
*Trichophyton mentagrophytes*
Algae
*Chlorella pyrenoidosa*
*Euglena gracilis*
*Scenedesmus obliquus*

TABLE I

In Vitro Agar Screening Tests
Minimum Inhibitory Concentration, µg/ml

| | Compound No. 1 |
|---|---|
| Bacteria | |
| Bacillus cereus | 50 |
| Brevibacterium ammoniagenes | (50) |
| Enterobacter aerogenes | 50 |
| Escherichia coli | >50 |
| Pseudomonas aeruginosa | >50 |
| Pseudomonas fluorescens | >50 |
| Fungi | |
| Aspergillus fumigatus | 50 |
| Aspergillus niger | 5 |
| Aspergillus oryzae | 50 |
| Pencillium expansum | 50 |
| Pencillium ochra-chloron | 50 |
| Pencillium vermiculatum | (5) |
| Rhizopus stolonifer | (10) |
| Trichoderma sp. | 50 |

TABLE I-continued

In Vitro Agar Screening Tests
Minimum Inhibitory Concentration, µg/ml

|  | Compound No. 1 |
|---|---|
| Trichophyton mentagrophytes | 50 |
| Algae |  |
| Chlorella pyrenoidosa | 1 |
| Euglena gracilis | 5 |
| Scenedesmus obliquus | 1 |

( ) = indicates partial control at this concentration, complete control at next higher concentration
> = greater than

EXAMPLE 3

Sulfate Reducing Bacteria In Vitro Test

This test measures the bactericidal properties of a compound when in contact with a sulfate reducing bacteria, specifically *Desulfovibrio desulfuricans*. The test is conducted by dissolving the test compound in acetone to give an 0.5% solution. This toxicant is added to vials containing sterile Sulfate API broth with tryptone under anaerobic conditions at such levels to give final toxicant concentrations of 1, 5, 10 and 50 µg/ml of solution. An inoculant solution of 0.5 ml of the growing organism, *Desulfovibrio desulfuricans*, is added to the vials followed by sufficient sterile distilled water to give a total of 10 ml of solution in the vials. The vials are incubated at room temperature for 3 to 5 days until untreated controls show growth of the organism as indicated by the black color development in the vials.

The following is a summary of the minimum inhibitory concentration necessary to control the organism.

TABLE II

|  | Compound No. 1 (µg/ml) |
|---|---|
| Desulfovibrio desulfuricans | (5) |

( ) = indicates partial control at this concentration, complete control at next higher concentration

EXAMPLE 4

Staphylococcus Aureus Use Dilution Test

This test measures the bacteriostatic effectiveness of a particular test compound against *Staphylococcus aureus*.

Tryptic Soy Broth is dispensed aseptically into sterile 13 × 100 mm clear glass culture tubes. The first tube receives 3.6 ml of medium and tubes 2 through 10 receive 2.0 ml of medium. The test compound is dissolved in acetone to give 10 ml of a solution of 0.10% of the test compound. Using a sterile syringe, 0.4 ml of the test compound solution is placed in the first tube containing the 3.6 ml of sterile broth and mixed thoroughly. This operation is continued through to the tenth tube. From the tenth tube, 2.0 ml of solution is removed and discarded. Each tube is then inoculated with 0.1 ml of a 24-hour culture of *Staphylococcus aureus* in Tryptic Soy Broth, and the mixture is mixed thoroughly using a Vortex mixer. A control is also set up to be sure that the inoculum is viable using a tube of sterile broth containing no added toxicant. The tubes are incubated for 24 hours at 37°C. The tubes are then examined to determine growth of the organism in the culture tubes. The minimum concentration in which no growth of the organism occurs is recorded. The following table gives the minimum inhibitory concentration necessary to control the organism:

TABLE III

| Toxicant | Minimum Inhibitory Concentration Staphylococcus aureus, µg/ml |
|---|---|
| Compound No. 1 | 12.5 |

The compound of this invention is generally embodied into a form suitable for convenient application. For example, the compound can be embodied into pesticidal compositions which are provided in the form of emulsions, suspensions, solution, dusts, and aerosol sprays. In general, such compositions will contain, in addition to the active compound, the adjuvants which are found normally in pesticide preparations. In these compositions, the active compound of this invention can be employed as the sole pesticide component or can be used in admixture with other compounds having similar utility. The pesticide compositions of this invention can contain, as adjuvants, organic solvents such as sesame oil, xylene range solvents, heavy petroleum, etc.; water; emulsifying agents; surface active agents; talc; pyrophyllite; diatomite; gypsum; clays; propellants, such as dichlorodifluoromethane, etc. In connection with the activity of the presently disclosed pesticidal compound, it should be fully understood that it is not necessary that it be active as such. The purposes of this invention will be fully served if the compound is rendered active by external influences, such as light or by some physiological action which occurs when the compound is ingested into the body of the pest.

The precise manner in which the pesticidal compositions of this invention are used in any particular instance will be readily apparent to a person skilled in the art. Generally, the active pesticide compound will be embodied in the form of a liquid composition; for example, an emulsion, suspension or aerosol spray. While the concentration of the active pesticide in the present pesticidal compositions can vary within rather wide limits, ordinarily the pesticide compound will comprise not more than about 15.0% by weight of the pesticidal composition. Preferably, however, the pesticidal compositions of this invention will be in the form of solutions or suspensions containing about 0.1 to 1.0% by weight of the active pesticide compound.

The compounds of this invention are also effective in controlling the growth and occurrence of slime-forming microorganisms whose formation are a problem in aqueous systems such as lagoons, lakes, ponds, pools, cooling water systems, and pulp and paper mill systems. Such control is achieved by adding the compound to the particular system being treated in a quantity adequate to control the slime-forming microorganisms which are contained by, or which may become entrained in, the system which is treated.

The compounds of this invention can be stabilized by the addition of epichlorohydrin, of which approximately 1% by weight is sufficient.

What is claimed:
1. A compound having the formula

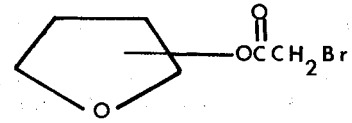

2. A stabilized composition consisting of the compound according to claim 1 and a stabilizing amount of epichlorohydrin.

3. A compound according to claim 1 in which the compound is 3-bromoacetoxy tetrahydrofuran.

4. A stabilized composition consisting of the compound according to claim 3 and a stabilizing amount of epichlorohydrin.

* * * * *